United States Patent
Yi et al.

(10) Patent No.: US 11,529,306 B2
(45) Date of Patent: Dec. 20, 2022

(54) LYOPHILIZED FORMULATION OF STEM CELL-DERIVED EXOSOMES AND ANTI-INFLAMMATORY COMPOSITION INCLUDING THE SAME AS ACTIVE INGREDIENT

(71) Applicant: ExoCoBio Inc., Seoul (KR)

(72) Inventors: Yong Weon Yi, Seoul (KR); Byong Seung Cho, Gunpo-si (KR); Kwang Il Kim, Goyang-si (KR)

(73) Assignee: ExoCoBio Inc., Seoul (KR)

( * ) Notice: Subject to any disclaimer, the term of this patent is extended or adjusted under 35 U.S.C. 154(b) by 284 days.

(21) Appl. No.: 16/913,624

(22) Filed: Jun. 26, 2020

(65) Prior Publication Data

US 2020/0323768 A1  Oct. 15, 2020

Related U.S. Application Data

(63) Continuation of application No. PCT/KR2019/008850, filed on Jul. 17, 2019.

(30) Foreign Application Priority Data

Jul. 30, 2018 (KR) .................. 10-2018-0088354
Mar. 26, 2019 (KR) .................. 10-2019-0034695

(51) Int. Cl.
| | |
|---|---|
| *A61K 8/98* | (2006.01) |
| *A61K 8/04* | (2006.01) |
| *A61K 8/73* | (2006.01) |
| *A61K 8/92* | (2006.01) |
| *A61K 9/19* | (2006.01) |
| *A61K 35/28* | (2015.01) |
| *A61Q 19/00* | (2006.01) |
| *A61K 9/00* | (2006.01) |

(52) U.S. Cl.
CPC .............. *A61K 8/981* (2013.01); *A61K 8/044* (2013.01); *A61K 8/735* (2013.01); *A61K 8/925* (2013.01); *A61K 9/19* (2013.01); *A61K 35/28* (2013.01); *A61Q 19/00* (2013.01); *A61K 9/0019* (2013.01); *A61K 2800/70* (2013.01); *A61K 2800/74* (2013.01); *A61K 2800/84* (2013.01); *A61K 2800/86* (2013.01); *A61K 2800/91* (2013.01)

(58) Field of Classification Search
None
See application file for complete search history.

(56) References Cited

U.S. PATENT DOCUMENTS

| | | |
|---|---|---|
| 9,180,098 B2 | 11/2015 | Hafner et al. |
| 2010/0297231 A1 | 11/2010 | Vehring et al. |
| 2013/0259896 A1 | 10/2013 | Khandke et al. |
| 2013/0315987 A1 | 11/2013 | Lu |
| 2016/0367660 A1 | 12/2016 | Hafner et al. |
| 2017/0087187 A1 | 3/2017 | Chang et al. |
| 2017/0209365 A1 | 7/2017 | Cho et al. |
| 2018/0332951 A1 | 11/2018 | Jang et al. |
| 2019/0030079 A1 | 1/2019 | Cho et al. |
| 2020/0121722 A1 | 4/2020 | Yi et al. |
| 2020/0329697 A1 | 10/2020 | Kim et al. |
| 2021/0077379 A1 | 3/2021 | Cho et al. |

FOREIGN PATENT DOCUMENTS

| | | |
|---|---|---|
| CN | 1160582 A | 10/1997 |
| CN | 106701672 A | 5/2017 |
| CN | 107006452 A | 8/2017 |
| EP | 3363817 A1 | 8/2018 |
| ER | 3 199 175 A1 | 8/2017 |
| JP | 2012-136518 A | 7/2012 |
| JP | 2015-057383 A | 3/2015 |
| JP | 2015-78177 A | 4/2015 |
| KR | 10-2015-0108795 A | 9/2015 |
| KR | 10-1663912 B1 | 10/2016 |
| KR | 10-2017-0089404 A | 8/2017 |
| KR | 10-2018-0042217 A | 4/2018 |
| KR | 10-2019-0069301 A | 6/2019 |
| WO | 96/09037 A1 | 3/1996 |
| WO | 98/36736 A1 | 8/1998 |
| WO | 2008/040556 A1 | 4/2008 |
| WO | 2010/148337 A1 | 12/2010 |
| WO | 2016/197196 A1 | 12/2016 |
| WO | 2017/015622 A2 | 1/2017 |

(Continued)

OTHER PUBLICATIONS

CN106701672A (English translation provided by Google). (Year: 2017).*
International Search Report of PCT/KR2019/005680 dated Aug. 16, 2019 [PCT/ISA/210].
International Search Report of PCT/KR2019/008832 dated Oct. 29, 2019 [PCT/ISA/210].
Naver Blog, "Get a regeneration care by EXOSOME ORIGINAL REPAIR ampule after Fraxel treatment / Stem Cell ampule / Fraxel treatment", Oct. 22, 2015, https://blog.naver.com/restemkorea/220516198077.
Bosch et al., "Trehalose prevents aggregation of exosomes and cryodamage", Scientific Reports, 2016, vol. 6, No. 36162, pp. 1-11 (12 pages total).
Ho Seong Jeon, "Improved Stability of Sterically Stabilized Liposomal Preparations by Lyophilization", Master's Thesis. Graduate School of Chung-ang University, Dec. 2000.

(Continued)

*Primary Examiner* — Michael Barker
(74) *Attorney, Agent, or Firm* — Sughrue Mion, PLLC

(57) ABSTRACT

The lyophilized formulation of stem cell-derived exosomes and the anti-inflammatory composition including the same as an active ingredient is able to stabilize stem cell-derived exosomes and exhibit excellent anti-inflammatory effects, and particularly, exhibit remarkable anti-inflammatory effects as compared with not-lyophilized stem cell-derived exosomes isolated and purified from conditioned media of stem cells. Therefore, the lyophilized formulation of stem cell-derived exosomes and the anti-inflammatory composition including the same as an active ingredient is able to effectively prevent, suppress, alleviate, ameliorate or treat inflammatory response or inflammatory diseases.

28 Claims, 22 Drawing Sheets

(56) References Cited

FOREIGN PATENT DOCUMENTS

| WO | 2017/020034 A1 | 2/2017 |
| WO | 2017/117585 A1 | 7/2017 |
| WO | 2017/122095 A1 | 7/2017 |
| WO | 2018/027075 A1 | 2/2018 |
| WO | 2018/050872 A1 | 3/2018 |
| WO | 2018/053004 A2 | 3/2018 |
| WO | 2018/070939 A1 | 4/2018 |
| WO | 2018/078524 A1 | 5/2018 |

OTHER PUBLICATIONS

International Search Report for PCT/KR2019/008850 dated Oct. 24, 2019 [PCT/ISA/210].

\* cited by examiner

LYOPHILIZED FORMULATION OF STEM CELL-DERIVED EXOSOMES AND ANTI-INFLAMMATORY COMPOSITION INCLUDING THE SAME AS ACTIVE INGREDIENT

CROSS REFERENCE

This application is a Bypass Continuation of International Application No. PCT/KR2019/008850 filed Jul. 17, 2019, claiming priority based on Korean Patent Application No. 10-2018-0088354 filed Jul. 30, 2018 and Korean Patent Application No. 10-2019-0034695 filed Mar. 26, 2019, the entire contents of which are incorporated herein by reference.

TECHNICAL FIELD

The present invention relates to a lyophilized formulation of stem cell-derived exosomes, which is used for the prevention, suppression, alleviation, amelioration or treatment of inflammation, and an anti-inflammatory composition including the same as an active ingredient.

Moreover, the present invention relates to a method of preventing, suppressing, alleviating, ameliorating or treating inflammatory diseases using the anti-inflammatory composition.

BACKGROUND ART

Inflammation is a defense response of the body against physical or chemical injury, infection of bacteria, fungi or viruses, or pathological conditions caused by various allergens and the like. Inflammatory response appears as part of innate immune response. Various substances and physiological and chemical phenomena are involved in inflammatory response, and recent studies have shown that various inflammatory cytokines play an important role in inflammatory response. Major cytokines involved in inflammatory response include IL-1$\beta$, TNF-$\alpha$, IL-6, IL-8, IL-12, IFN-$\beta$, and the like. The increased expression and secretion of these cytokines and the activation thereof are associated with a series of complex physiological responses, including secretion of inflammatory mediators, immune cell infiltration, cell migration, and tissue destruction, as well as symptoms such as erythema, edema, fever and pain.

In general, inflammatory response does not become a significant problem and the affected area returns to its normal state, if the infectious agent is removed from the body and the damaged tissue is regenerated. However, if the infectious agent is not removed from the body or the inflammatory response is excessive or persistent due to internal substances of the body, acute or chronic inflammatory disease occurs.

Immunosuppressive drugs, such as non-steroidal anti-inflammatory drugs, steroidal anti-inflammatory drugs, antagonists of neuropeptides, COX inhibitors, anti-histamines, and cyclosporine A, are used for the alleviation or treatment of inflammatory response or inflammatory diseases caused thereby, but have problems that they cause adverse effects such as skin atrophy, vasodilation, depigmentation, hypersensitivity reactions, tolerance, neutropenia and the like. In addition, there is a limit that the aforesaid drugs merely help to control symptoms related to inflammation to a certain level rather than the underlying treatment therefor.

In recent years, studies have been actively conducted on the development of inflammatory disease therapeutics or functional cosmetics using natural substances. In the case of inflammatory disease therapeutics or functional cosmetics based on these natural substances, the amount of an active ingredient in the natural extract is low, and hence a large amount of the natural extract needs to be used to obtain the anti-inflammatory effect. In the majority of cases, the fact that these therapeutics or functional cosmetics are based on natural substances has been emphasized in marketing, but there is a need for more scientific research on the practical efficacies of natural substances on the anti-inflammatory effect.

Recently, there have been reports that cell secretomes contain various bioactive molecules that regulate cellular behaviors. In particular, cell secretomes contain 'exosome' that has intercellular signaling functions, and thus studies on the components and functions thereof have been actively conducted.

Cells shed various membraneous vesicles to their extracellular environment, and these released vesicles are usually called extracellular vesicles (EVs). The EV is also called cell membrane-derived vesicle, ectosome, shedding vesicle, microparticle, exosome, etc., and is also used discriminately from exosome in some cases.

Exosome is a vesicle of tens to hundreds of nanometers in size, which consists of a phospholipid bilayer membrane having the same structure as that of the cell membrane. This exosome contains proteins, nucleic acids (mRNA, miRNA, etc.) and the like which are called exosome cargo. It is known that exosome cargo includes a wide range of signaling factors, and these signaling factors are specific for cell types and regulated differently depending on secretory cells' environment. It is known that exosome is an intercellular signaling mediator secreted by cells, and various cellular signals transmitted through it regulate cellular behaviors, including the activation, growth, migration, differentiation, dedifferentiation, apoptosis, and necrosis of target cells. Exosome contains specific genetic materials and bioactive factors depending on the nature and state of cells from which the exosome was derived. Exosome derived from proliferating stem cells regulates cell behaviors such as cell migration, proliferation and differentiation, and recapitulates the characteristics of stem cells involved in tissue regeneration (Nature Review Immunology 2002 (2) 569-579).

That is, exosomes called "avatars" of cells contain bioactive factors, such as growth factors, similar to cells. However, when exosomes are stored at room temperature, their stability problems arise that the activity of bioactive factors contained therein is lowered. In addition, when exosomes are simply cold-stored, changes in the overall physical properties and stability of exosomes may occur depending on their storage time and method, and thus the activity of bioactive factors contained therein may also be lowered.

However, although various studies of exosomes have been conducted, which suggest the possibility for the treatment of some diseases using exosomes, not much attention has been paid to the development of new formulations which can stably maintain and make exosomes stored, and the linking of exosomes with various medical or cosmetic technologies for increasing the convenience and efficacy of exosomes.

The present inventors have conducted extensive studies on the development of a novel formulation capable of stably maintaining and storing stem cell-derived exosomes and on the application of this formulation to medical or cosmetic technology, and as a result, have developed a lyophilized formulation of stem cell-derived exosomes, which stabilizes stem cell-derived exosomes and exhibits an excellent anti-inflammatory effect, and an anti-inflammatory composition including the same, thereby completing the present invention.

Meanwhile, it is to be understood that the matters described as the background art are intended merely to aid in the understanding of the background of the present invention and are not admitted as prior art against the present invention.

SUMMARY OF INVENTION

An object of the present invention is to provide a lyophilized formulation of stem cell-derived exosomes, which is used for the prevention, suppression, alleviation, amelioration or treatment of inflammation, and an anti-inflammatory composition including the same as an active ingredient.

Another object of the present invention is to provide an anti-inflammatory pharmaceutical composition, functional cosmetic composition and skin external preparation including the above anti-inflammatory composition.

Still another object of the present invention is to provide a method of preventing, suppressing, alleviating, ameliorating or treating inflammatory diseases using the above anti-inflammatory composition.

However, the objects of the present invention as described above are illustrative and the scope of the present invention is not limited thereby. In addition, other objects and advantages of the present invention will be more apparent from the following description, the appended claims and the accompanying drawings.

DETAILED DESCRIPTION OF INVENTION

The present invention provides a lyophilized formulation of stem cell-derived exosomes, which is used for the prevention, suppression, alleviation, amelioration or treatment of inflammation, and an anti-inflammatory composition including the same as an active ingredient.

As used herein, the term "exosomes" refers to vesicles of tens to hundreds of nanometers in size (preferably, about 30 to 200 nm), which consist of a phospholipid bilayer membrane having the same structure as that of the cell membrane (however, the particle size of exosomes is variable depending on the type of cell from which the exosomes are isolated, an isolation method and a measurement method) (Vasiliy S. Chernyshev et al., "Size and shape characterization of hydrated and desiccated exosomes", Anal Bioanal Chem, (2015) DOI 10.1007/s00216-015-8535-3). These exosomes contain proteins, nucleic acids (mRNA, miRNA, etc.) and the like which are called exosome cargo. It is known that exosome cargo includes a wide range of signaling factors, and these signaling factors are specific for cell types and regulated differently depending on secretory cells' environment. It is known that exosomes are intercellular signaling mediators secreted by cells, and various cellular signals transmitted through them regulate cellular behaviors, including the activation, growth, migration, differentiation, dedifferentiation, apoptosis, and necrosis of target cells.

Meanwhile, the term "exosomes" as used herein is intended to include all vesicles (e.g., exosome-like vesicles) which are secreted from stem cells and released into extracellular spaces, and have a nano-sized vesicle structure and a composition similar to that of exosomes. The stem cells are not limited to the kind thereof, but may preferably be mesenchymal stem cells, for example, adipose-, bone marrow-, umbilical cord- or umbilical cord blood-derived stem cells, more preferably adipose-derived stem cells. The adipose-derived stem cells are not limited to the kind thereof as long as they have no risk of infection with pathogens and do not cause immune rejection, but may preferably be human adipose-derived stem cells.

However, as exosomes used in the present invention, various exosomes that are being used in the art or may be used in the future may, of course, be used as long as they have an anti-inflammatory effect and do not cause adverse effects on the human body. Therefore, it should be noted that exosomes isolated according to the isolation method of Examples described below should be understood as an example of exosomes that may be used in the present invention, and the present invention is not limited thereto.

As used herein, the term "iontophoresis" refers to a method of flowing a microcurrent through a skin to which an active ingredient has been applied, generating a potential difference thereby and changing the electrical environment of the skin, and thus allowing an ionized active ingredient to penetrate the skin by electrical repulsion. Examples of iontophoresis that is used in one embodiment of the present invention include: a method of introducing a microcurrent into a skin by allowing the microcurrent to flow from an external power source into an electrode patch on the skin, the microcurrent generated by the external power source; a method of introducing a microcurrent into a skin, the microcurrent generated by a battery provided in an electrode patch on the skin; and a method of introducing a microcurrent into a skin through a patch on the skin provided with a reverse electrodialysis device, the microcurrent generated by the concentration difference between high concentration electrolyte solution and low concentration electrolyte solution in the reverse electrodialysis device. However, the present invention is not limited thereto, and various types of iontophoresis may, of course, be used.

The anti-inflammatory composition of the present invention is used for the prevention, suppression, alleviation, amelioration or treatment of inflammatory diseases. As an example, not limiting the present invention, examples of the inflammatory diseases include dermatitis, atopic dermatitis, eczema, inflammation caused by bacterial, viral or fungal infections, burns, inflammation caused by burns, wounds, inflammation caused by wounds, ulcerative colitis, arthritis, rheumatoid arthritis, hepatitis, nephritis, and the like.

The present invention also provides a lyophilized formulation of stem cell-derived exosomes for prevention, suppression, alleviation, amelioration or treatment of inflammation comprising: as active ingredients, stem cell-derived exosomes; and methionine, mannitol, and trehalose. For example, the weight ratio of methionine, mannitol and trehalose in the lyophilized formulation may be 1:1:1.

The lyophilized formulation of stem cell-derived exosomes according to one embodiment of the present invention may further comprise ascorbic acid and retinol. For example, the weight ratio of methionine, mannitol, trehalose, ascorbic acid and retinol in the lyophilized formulation may be 9:9:9:0.5:0.5.

The anti-inflammatory composition according to one embodiment of the present invention may comprise the lyophilized formulation of stem cell-derived exosomes and a diluent. For example, the diluent may be water for injection, physiological saline, phosphate buffered saline, purified water, or deionized water. In addition, the diluent may further comprise hyaluronic acid or hyaluronate (e.g., sodium hyaluronate). For example, the anti-inflammatory composition may be prepared as a suspension.

In one embodiment of the present invention, the anti-inflammatory composition may be administered by microneedling, iontophoresis or injection.

In one embodiment of the present invention, the anti-inflammatory composition may be a pharmaceutical composition, a cosmetic composition or a skin external preparation. For example, the anti-inflammatory composition may be prepared as an injectable formulation.

In one embodiment of the present invention, when the anti-inflammatory composition is used as a pharmaceutical composition, it may include pharmaceutically acceptable carriers, excipients or diluents. The carriers, excipients and dilutes include, but are not limited to, lactose, dextrose, trehalose, sucrose, sorbitol, mannitol, xylitol, erythritol, maltitol, starch, acacia gum, alginate, gelatin, calcium phosphate, calcium carbonate, calcium silicate, cellulose, methyl cellulose, microcrystalline cellulose, polyvinyl pyrrolidone, water, methyl hydroxybenzoate, propyl hydroxybenzoate, talc, magnesium stearate, and mineral oil. In addition, the effective amount of the pharmaceutical composition according to one embodiment of the present invention means the amount required for administration in order to achieve an anti-inflammatory effect.

The content of the pharmaceutical composition according to one embodiment in a formulation may be suitably selected depending on the kind, amount, form and the like of additional components as described above. For example, the pharmaceutical composition of the present invention may be contained in an amount of about 0.1 to 99 wt %, preferably about 10 to 90 wt %, based on the total weight of an injectable formulation. Furthermore, the suitable dose of the pharmaceutical composition according to one embodiment of the present invention may be adjusted depending on the kind of inflammatory disease, the severity of inflammatory disease, the type of formulation, formulating method, patient's age, sex, body weight, health condition, diet, excretion rate, the period of administration, and the regime of administration. For example, when the pharmaceutical composition according to one embodiment of the present invention is administered to an adult, it may be administered once to several times at a dose of 0.001 mg/kg to 100 mg/kg per day.

Meanwhile, when the anti-inflammatory composition according to one embodiment of the present invention is prepared as a skin external preparation and/or a cosmetic composition, it may suitably contain components which are generally used in cosmetic products or skin external preparations, for example, moisturizers, antioxidants, oily components, UV absorbers, emulsifiers, surfactants, thickeners, alcohols, powder components, colorants, aqueous components, water, and various skin nutrients, etc., as needed, within the range that does not impair the effect of the present invention.

Furthermore, the skin external preparation and/or cosmetic composition according to one embodiment of the present invention may comprise, in addition to the lyophilized formulation of stem cell-derived exosomes or the anti-inflammatory composition comprising the same, an anti-inflammatory agent and/or an antiphlogistic drug, which has been used in the prior art, within the range that does not impair the effects (e.g., anti-inflammatory effect) thereof. For example, the lyophilized formulation of stem cell-derived exosomes or the anti-inflammatory composition comprising the same may be contained in or mixed with at least one of hydrogel, hyaluronic acid, salt of hyaluronic acid (e.g., sodium hyaluronate, etc.), or hyaluronate gel. In the skin external preparation and/or cosmetic composition according to one embodiment of the present invention, the kind of hydrogel is not particularly limited, but the hydrogel may be preferably obtained by dispersing a gelled polymer in a polyhydric alcohol. The gelled polymer may be at least one selected from the group consisting of pluronic, purified agar, agarose, gellan gum, alginic acid, carrageenan, cassia gum, xanthan gum, galactomannan, glucomannan, pectin, cellulose, guar gum, and locust bean gum, and the polyhydric alcohol may be at least one selected from the group consisting of ethylene glycol, propylene glycol, 1,3-butylene glycol, isobutylene glycol, dipropylene glycol, sorbitol, xylitol, and glycerin.

The skin external preparation and/or cosmetic composition according to one embodiment of the present invention may be used in various forms, for example, patches, mask packs, mask sheets, creams, tonics, ointments, suspensions, emulsions, pastes, lotions, gels, oils, packs, sprays, aerosols, mists, foundations, powders, and oilpapers. For example, the skin external preparation and/or cosmetic composition may be applied to or soaked in at least one surface of a patch, a mask pack or a mask sheet.

The cosmetic composition according to one embodiment of the present invention is used for the purpose of preventing, suppressing, alleviating or ameliorating inflammation, and the cosmetic composition may be prepared as any formulation which is generally prepared in the art. For example, it may be formulated as patch, mask pack, mask sheet, skin softener, nutrition, astringent lotion, nourishing cream, massage cream, eye cream, cleansing cream, essence, eye essence, cleansing lotion, cleansing foam, cleansing water, sunscreen, lipstick, soap, shampoo, surfactant-containing cleanser, bath preparation, body lotion, body cream, body oil, body essence, body cleanser, hairdye, hair tonic, etc., but is not limited thereto.

The skin external preparation and/or cosmetic composition according to one embodiment of the present invention contains components which are commonly used in skin external preparations and/or cosmetic products. For example, the skin external preparation and/or cosmetic composition may contain conventional adjuvants and carriers, such as antioxidants, stabilizers, solubilizers, vitamins, pigments, and fragrances. In addition, other components in each formulation for the skin external preparation and/or cosmetic composition may be suitably selected without difficulty by those skilled in the art depending on the type or intended use of skin external preparation and/or cosmetic composition.

The present invention also provides a method of preventing, suppressing, alleviating, ameliorating or treating inflammatory diseases using the anti-inflammatory composition.

The method of preventing, suppressing, alleviating, ameliorating or treating inflammatory diseases according to one embodiment of the present invention includes steps of: (a) preparing the anti-inflammatory composition; and (b) treating an inflammatory area of a subject with the anti-inflammatory composition.

In the method of preventing, suppressing, alleviating, ameliorating or treating inflammatory diseases according to one embodiment of the present invention, the anti-inflammatory composition may be administered to a mammalian skin by microneedling, iontophoresis or injection.

The method of preventing, suppressing, alleviating, ameliorating or treating inflammatory diseases according to one embodiment of the present invention further includes steps of: (c) performing iontophoresis by allowing a microcurrent to flow through the skin treated with the anti-inflammatory composition; and (d) delivering the anti-inflammatory composition inside the skin by the microcurrent.

In the method of preventing, suppressing, alleviating, ameliorating or treating inflammatory diseases according to one embodiment of the present invention, the anti-inflammatory composition may be used in various forms, for example, patches, mask packs, mask sheets, creams, tonics, ointments, suspensions, emulsions, pastes, lotions, gels, oils, packs, sprays, aerosols, mists, foundations, powders, and oilpapers. For example, the anti-inflammatory composition may be applied to or soaked in at least one surface of a patch, a mask pack or a mask sheet.

In the method of preventing, suppressing, alleviating, ameliorating or treating inflammatory diseases according to one embodiment of the present invention, step (b) may be performed by: (b1) applying the anti-inflammatory composition directly to the skin; or (b2) contacting or attaching a mask pack, a mask sheet or a patch, which has the anti-inflammatory composition applied thereto or soaked therein, to the skin; or sequentially performing (b1) and (b2).

In the method of preventing, suppressing, alleviating, ameliorating or treating inflammatory diseases according to one embodiment of the present invention, at least one of hydrogel, hyaluronic acid, salts of hyaluronic acid (e.g., sodium hyaluronate, etc.), or hyaluronate gel may be applied to at least one side of the mask pack, mask sheet or patch. The kind of hydrogel is not limited, but the hydrogel may be preferably obtained by dispersing a gelled polymer in a polyhydric alcohol. The gelled polymer and the polyhydric alcohol may be those exemplified in the foregoing.

In the method of preventing, suppressing, alleviating, ameliorating or treating inflammatory diseases according to one embodiment of the present invention, step (c) may be performed by contacting or attaching an iontophoresis device to the skin.

In the method of preventing, suppressing, alleviating, ameliorating or treating inflammatory diseases according to one embodiment of the present invention, the iontophoresis device may include at least one battery selected from the group consisting of flexible batteries, lithium-ion secondary batteries, alkaline batteries, dry cells, mercury batteries, lithium batteries, nickel-cadmium batteries, and reverse electrodialysis batteries.

Advantageous Effects

The lyophilized formulation of stem cell-derived exosomes and the anti-inflammatory composition including the same as an active ingredient according to the present invention is able to stabilize stem cell-derived exosomes and exhibit excellent anti-inflammatory effects, and particularly, exhibit remarkable anti-inflammatory effects as compared with not-lyophilized stem cell-derived exosomes isolated and purified from conditioned media of stem cells.

Therefore, the lyophilized formulation of stem cell-derived exosomes and the anti-inflammatory composition including the same as an active ingredient is able to effectively prevent, suppress, alleviate, ameliorate or treat inflammatory response or inflammatory diseases.

It should be understood that the scope of the present invention is not limited to the aforementioned effects.

BRIEF DESCRIPTION OF DRAWINGS

"FIG. 1A" shows the particle size distribution and the number of particles obtained by nanoparticle tracking analysis (NTA). "FIG. 1B" shows particle images obtained by transmitted electron microscopy (TEM)". "FIG. 1C" shows the results of Western blot analysis for positive markers of stem cell-derived exosomes obtained according to one embodiment of the present invention. "FIG. 1D" shows the results of Western blot analysis for negative markers of stem cell-derived exosomes obtained according to one embodiment of the present invention. "FIG. 1E" shows the results of flow cytometry of CD9, CD63 and CD81 in the analysis of markers for stem cell-derived exosomes obtained according to one embodiment of the present invention.

In FIGS. 5 to 8, when RAW 264.7 cells were treated with different concentrations (expressed as the number of particles per mL) of stem cell-derived exosomes (exosomes isolated and purified from conditioned media of stem cells) prepared in Example 2, and then treated with LPS, the LPS-induced production of IL-1β, IL-6, IL-27 and IFN-β in the cells decreased in a manner of depending on the concentration of the exosomes.

In FIGS. 9 to 12, when RAW 264.7 cells were treated with different concentrations (expressed as the number of particles per mL) of aqueous solutions obtained and diluted by mixing a lyophilized formulation of stem cell-derived exosomes (prepared in Example 5-1) with a culture medium, and then treated with LPS, the LPS-induced production of IL-1β, IL-6, IL-27 and IFN-β in the cells remarkably decreased in a manner of depending on the concentration of the lyophilized formulation.

EXAMPLES

Figure 1A:
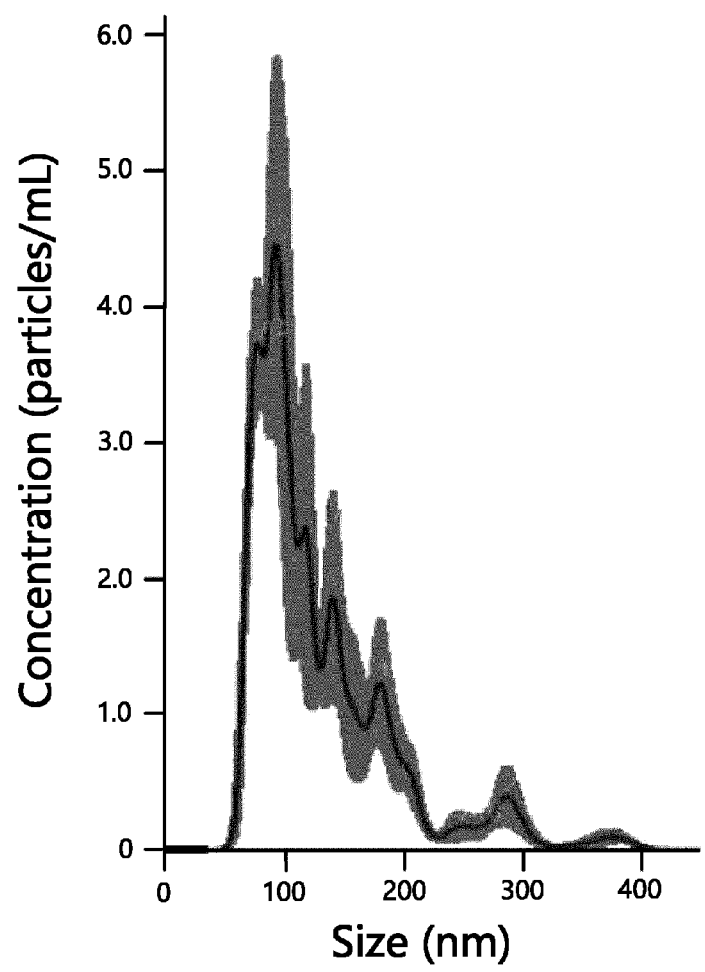
FIGS. 1A to 1E show the results of analyzing the physical properties of stem cell-derived exosomes obtained according to one embodiment of the present invention.

Hereinafter, the present invention will be described in more detail with reference to the following examples. However, the following examples are only to illustrate the present invention and are not intended to limit or restrict the scope of the present invention. Those that can be easily inferred by those skilled in the art from the detailed description and examples of the present invention are interpreted as falling within the scope of the present invention. References referred to in the present invention are incorporated herein by reference.

Throughout the present specification, it is to be understood that, when any part is referred to as "comprising" any component, it does not exclude other components, but may further include other components, unless otherwise specified.

Example 1: Cell Culture

Human dermal fibroblast (HDF) HS68 cells purchased from ATCC were subcultured in DMEM (purchased from ThermoFisher Scientific) medium containing 10% fetal bovine serum (FBS; purchased from ThermoFisher Scientific) and 1% antibiotics-antimycotics (purchased from ThermoFisher Scientific) at 37° C. under 5% $CO_2$.

According to a cell culture method known in the technical field to which the present invention pertains, adipose-derived stem cells were cultured at 37° C. under 5% $CO_2$. Next, the cells were washed with phosphate-buffered saline (purchased from ThermoFisher Scientific), and then the medium was replaced with serum-free, phenol red-free medium, and the cells were cultured for 1 to 10 days. The supernatant (hereinafter, referred to as "conditioned medium") was recovered.

In order to obtain exosomes having a uniform particle size distribution and high purity in an exosome isolation process, 2 wt % of trehalose was added to the conditioned medium. After addition of trehalose, the conditioned medium was filtered through 0.22 μm filter to remove impurities, such as cell debris, waste, macroparticles and the like. From the filtered conditioned medium, exosomes were immediately isolated. In addition, the filtered conditioned medium was stored in a refrigerator (10° C. or below), and then used for exosome isolation. Furthermore, the filtered conditioned medium was freeze-stored in an ultra-low temperature freezer at −60° C. or below, thawed, and then subjected to exosome isolation. Thereafter, exosomes were isolated from the conditioned medium by Tangential Flow Filtration (TFF).

Example 2: Isolation and Purification of Exosomes by TFF Method

For isolating, concentrating and diafiltrating exosomes from the conditioned medium filtered through 0.22 μm filter in Example 1, TFF method was used. As a filter for TFF method, a cartridge filter (known as a hollow fiber filter; purchased from GE Healthcare) or a cassette filter (purchased from Pall, Sartorius or Merck Millipore) was used. The TFF filter may be selected with various molecular weight cutoffs (MWCOs). Using the filter having selected MWCO, exosomes were isolated and concentrated, and particles, proteins, lipids, nucleic acids, low-molecular-weight compounds, etc., were removed, which are smaller than the MWCO.

To isolate and concentrate exosomes, a TFF filter having MWCO of 100,000 Da (Dalton), 300,000 Da or 500,000 Da was used. Exosomes were isolated from the conditioned medium by removing substances smaller than the MWCO and concentrating the conditioned medium to a volume of about 1/100 to 1/25 by the TFF method.

The isolated and concentrated solution of exosomes was additionally subjected to diafiltration. The diafiltration was performed continuously (continuous diafiltration) or discontinuously (discontinuous diafiltration), using a buffer having at least 4 times, preferably at least 6 to 10 times, more preferably at least 12 times volume of the starting volume. To obtain exosomes having a uniform particle size distribution and high purity, 2 wt % trehalose in PBS was added to the buffer.

Example 3: Analysis of Characteristics of Isolated Exosomes

Figure 1B:
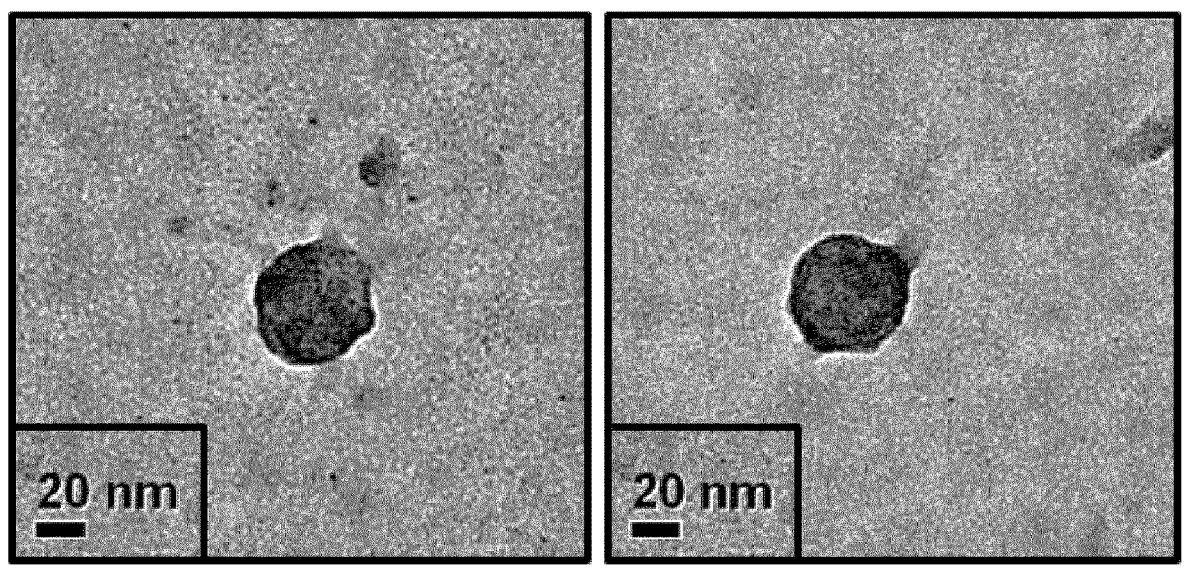

The particle size and concentration of the isolated exosomes were measured by nanoparticle tracking analysis (NTA) instrument (purchased from Malvern). The uniformity and size of the isolated exosomes were analyzed by transmission electron microscopy (TEM). FIGS. 1A and 1B show the results of NTA and TEM of the exosomes isolated by the isolation method according to one embodiment of the present invention.

Figure 1C:
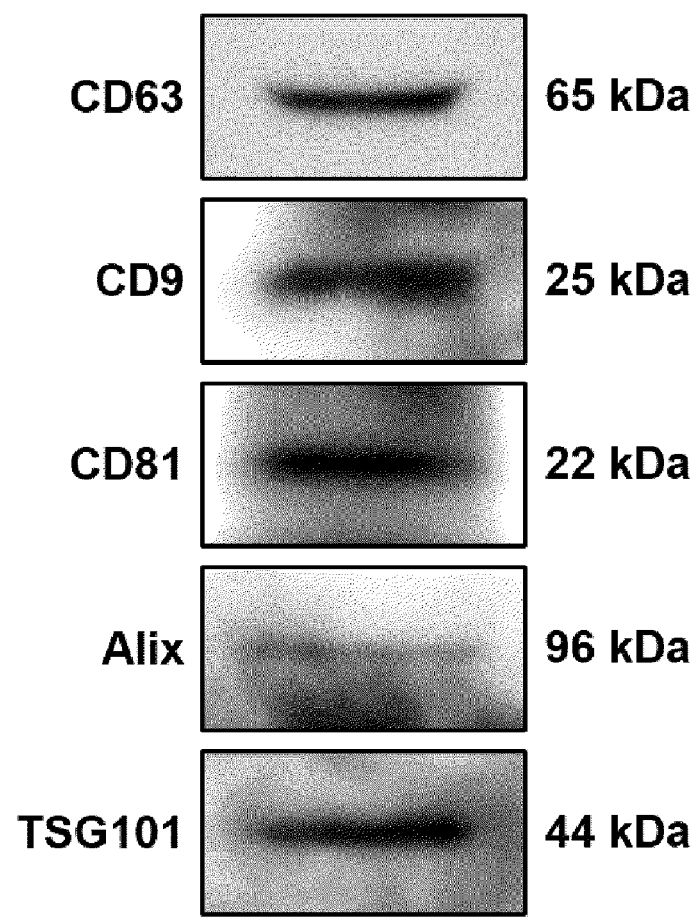

FIG. 1C shows the results of Western blot analysis for positive markers of the exosomes isolated by the isolation method according to one embodiment of the present invention. As shown therein, the presence of CD63, CD9, CD81, Alix and TSG101 markers was confirmed. As antibodies for each of the markers, anti-CD63, anti-CD9, anti-CD81, anti-Alix and anti-TSG101 were used, respectively.

Figure 1D:
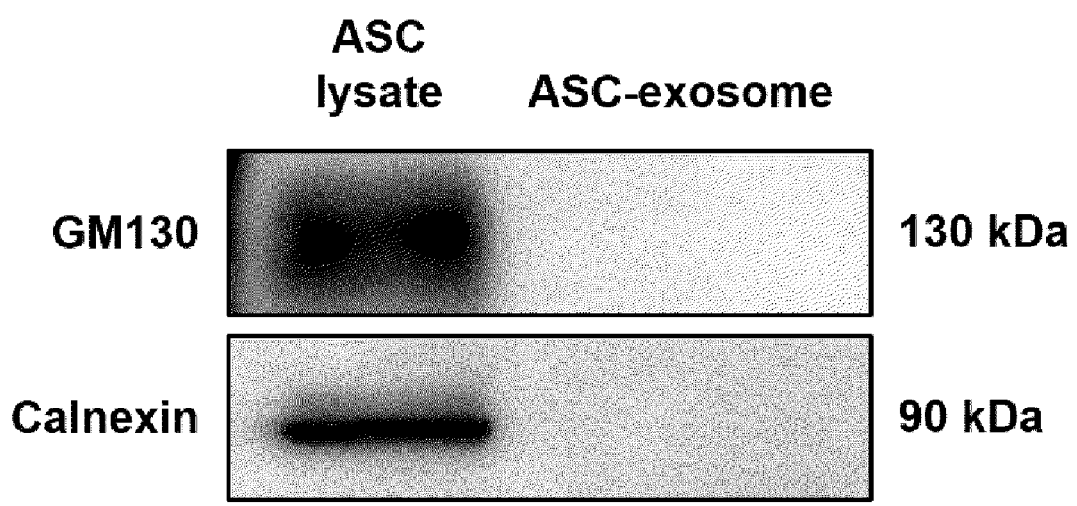

FIG. 1D shows the results of Western blot analysis for negative markers of the exosomes isolated by the isolation method according to one embodiment of the present invention. As antibodies for each of the markers, anti-GM130 and anti-Calnexin were used, respectively. GM130 and Calnexin are negative markers that should not be present in exosomes when the characteristics of the exosomes are analyzed. As shown in FIG. 1D, it was confirmed that GM130 and Calnexin were present in a lysate in adipose-derived stem cells, but were not present in the exosomes isolated by the isolation method according to one embodiment of the present invention. Therefore, when considering the results shown in FIGS. 1C and 1D together, it can be seen that the exosomes isolated by the isolation method according to one embodiment of the present invention are exosomes satisfying the characteristics of the positive markers and negative markers.

Figure 1E:
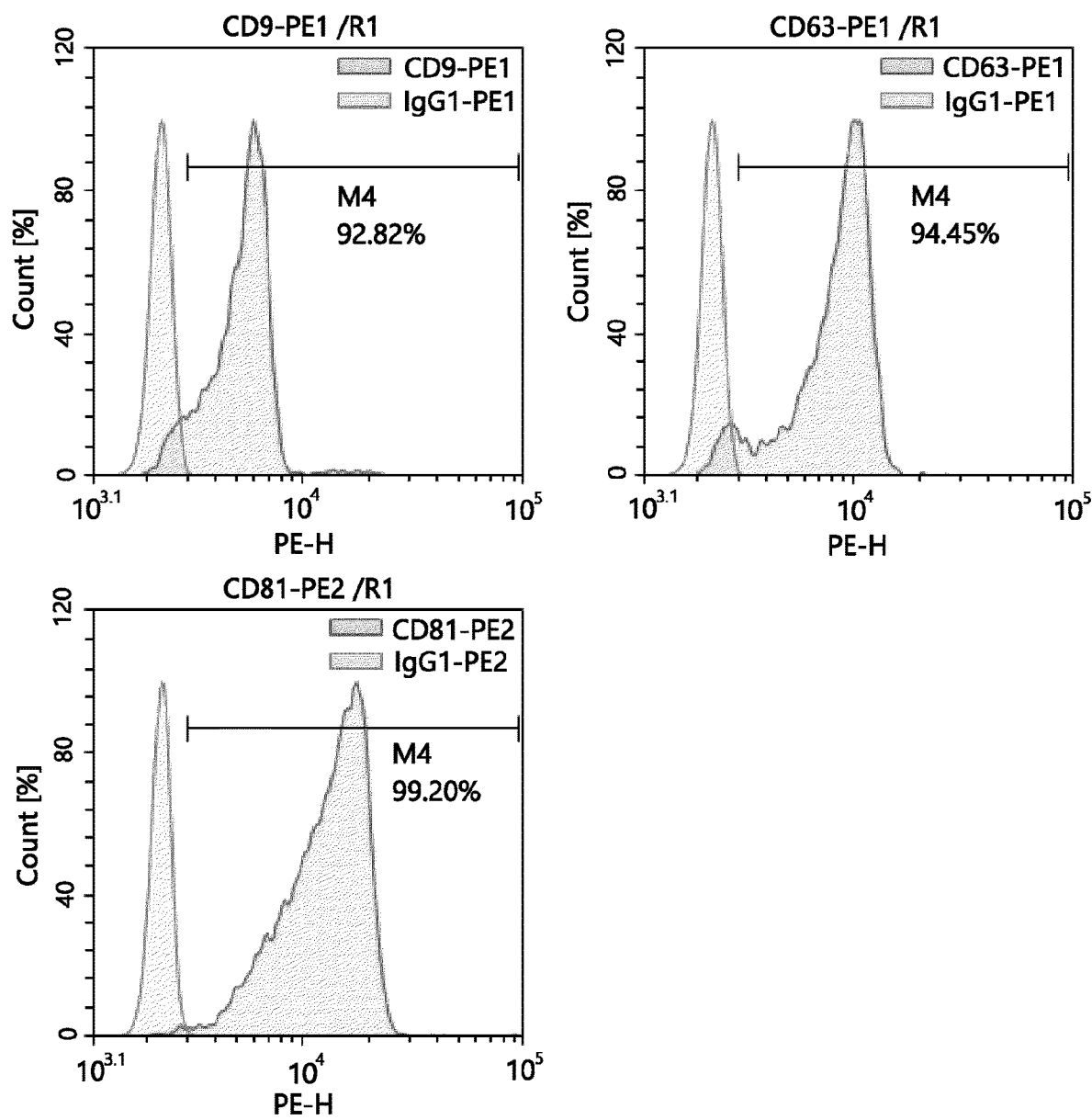

FIG. 1E shows the results of flow cytometry of the exosomes isolated by the isolation method according to one embodiment of the present invention. As shown therein, the presence of CD9, CD63 and CD81 markers was confirmed. To isolate CD81-positive exosomes, an Exosome-Human CD81 Isolation/Detection Reagent kit (purchased from ThermoFisher Scientific) was used according to the manufacturer's instruction. The markers were stained with PE-Mouse anti-human CD9 (purchased from BD), PE-Mouse anti-human CD63 (purchased from BD) or PE-Mouse anti-human CD81 (purchased from BD), and then analyzed using a flow cytometer (ACEA Biosciences).

Example 4: Measurement of Cytotoxicity Following Exosome Treatment

In order to evaluate the cytotoxicity of exosomes, isolated by the isolation method according to one embodiment of the present invention, in human skin fibroblast HS68 cells, the cells were treated with various concentrations of the exosomes, and the proliferation rate of the cells was examined. Specifically, HS68 cells were suspended in 10% FBS-containing DMEM, and then seeded resulting in 80 to 90% confluency and cultured in an incubator at 37° C. under 5% $CO_2$ for 24 hours. After 24 hours, the medium was removed, and the cells were treated with various concentrations of the exosomes prepared in Example 2. Then, the viability of the cells was evaluated while the cells were cultured for 24 to 72 hours. The cell viability was measured using WST-1 reagent (purchased from Takara), MTT reagent (purchased from Sigma), CellTiter-Glo reagent (purchased from Promega) or alamarBlue reagent (purchased from ThermoFisher Scientific) with a microplate reader (purchased from Molecular Devices).

Figure 2:
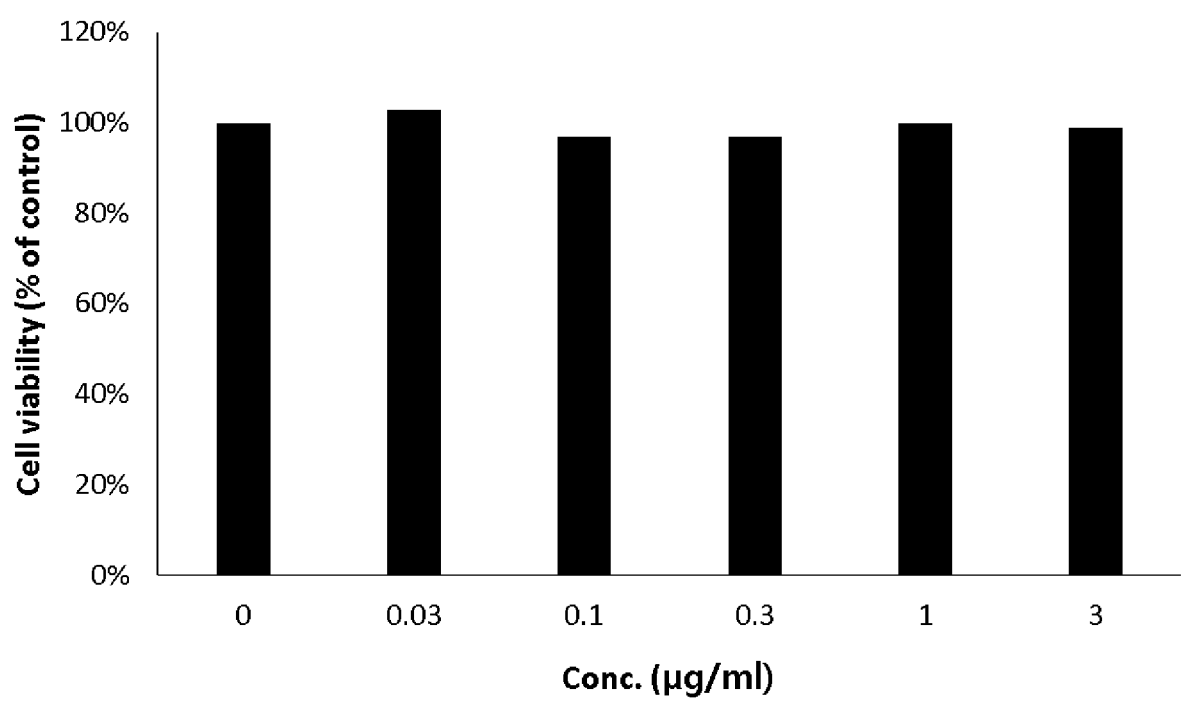
FIG. 2 shows results indicating that stem cell-derived exosomes according to one embodiment of the present invention were not cytotoxic after human fibroblast HS68 cells were treated with the exosomes.

As a control, the cells cultured in conventional cell culture medium not treated with the exosomes was used. It was confirmed that the exosomes of the present invention showed no cytotoxicity in the concentration range used in the test (FIG. 2).

Example 5: Lyophilization of Exosomes

Example 5-1: Lyophilization Conditions

For lyophilization of exosomes, a cryoprotectant comprising methionine, mannitol and trehalose was prepared. An aqueous solution was prepared by adding the cryoprotectant was added to 1 mL of an aqueous solution containing 0.5 mg/mL each of ascorbic acid and retinol (prepared by BIO-FD&C Co., Ltd., Hwasun-gun, Jeollanam-do, Korea). Although the cryoprotectant was added to the solution containing ascorbic acid and retinol in this Example, an aqueous solution may also be prepared by adding the cryoprotectant to water for injection, purified water, physical saline, or deionized water. The concentration of each of methionine, mannitol and trehalose in the aqueous solution was adjusted to 9 mg/mL.

The exosomes ($5\times10^8$ particles/mL) prepared in Example 2 were mixed with the aqueous solution containing the cryoprotectant, and then lyophilized using a lyophilization system (manufactured by VIRTIS, ITEM No.: 344424) under the conditions shown in Table 1 below. The lyophilization was performed in the order of conditions 1, 2, 3, 4, 5, 6, 7 and 8 as shown in Table 1 below.

TABLE 1

| Lyophilization conditions | | | |
|---|---|---|---|
| Total time (min) | | 4320 | |
| Conditions | Time (min) | Temperature (° C.) | Pressure (mmHg) |
| 1 | 700 | −50 | 760 |
| 2 | 60 | −50 | 760 |
| 3 | 999 | −50 | 0 |
| 4 | 999 | −50 | 0 |
| 5 | 999 | −50 | 0 |
| 6 | 370 | −50 | 0 |
| 7 | 120 | −20 | 0 |
| 8 | 73 | 10 | 0 |

Figure 3:
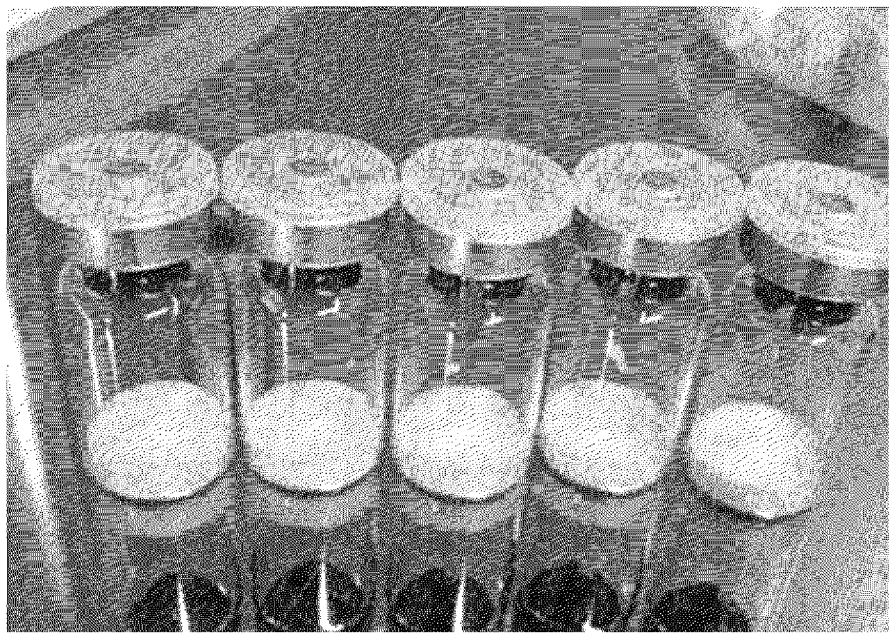
FIG. 3 depicts a photograph showing a good appearance of exosomes lyophilized according to one embodiment of the present invention.

After the exosomes were treated with the cryoprotectant comprising methionine, mannitol and trehalose, and lyophilized, the appearance thereof was examined. As a result, it can be seen that the exosomes were milky white in color and showed a good appearance which maintains a porous sponge shape (FIG. 3). That is, the method for lyophilizing exosomes according to the present invention is able to produce a lyophilized product having a good appearance by prolonging the drying time under vacuum and using the cryoprotectant having the combination of methionine, mannitol and trehalose.

Example 5-2: Comparison of Appearances of Lyophilized Exosomes Depending on Cryoprotectant Components Meanwhile, the appearances of exosomes lyophilized using various cryoprotectants comprising at least one of methionine, mannitol and trehalose (hereinafter, referred to as cryoprotectant components) were compared. According to the method described in Example 5-1 above, seven different aqueous solutions were prepared by adding the cryoprotectant components alone, combinations of two components, or a combination of three components. The concentration of each of the cryoprotectant components in each of the aqueous solutions was adjusted to 9 mg/mL. According to the lyophilization conditions and method described in Example 5-1 above, the exosomes ($5\times10^8$ particles) prepared in Example 2 above were mixed with the respective aqueous solution containing each of the cryoprotectant components alone, each of the combinations of two components, or the combination of three components, and then lyophilized.

The external appearances of the lyophilized exosome products were photographed and evaluated (FIGS. 4A to 4G). According to the states of the cake shapes of the lyophilized exosome products, the appearances of the lyophilized exosome products were ranked and relatively evaluated in a 5-point scale ranging from 1 (the worst cake appearance) to 5 (the best cake appearance). Table 2 below shows the results of evaluating the appearances of the lyophilized exosome products according to the combinations of the cryoprotectant components.

TABLE 2

Comparison of appearances of lyophilized exosome products according to combinations of cryoprotectant components

Figure 4A:
FIGS. 4A to 4G are photographs each of which shows, after performing lyophilization using different combinations of cryoprotectant components, the appearance of lyophilized exosomes obtained according to each of the combinations of cryoprotectant components.
Figure 4B:
Figure 4C:
Figure 4D:
Figure 4E:
Figure 4F:
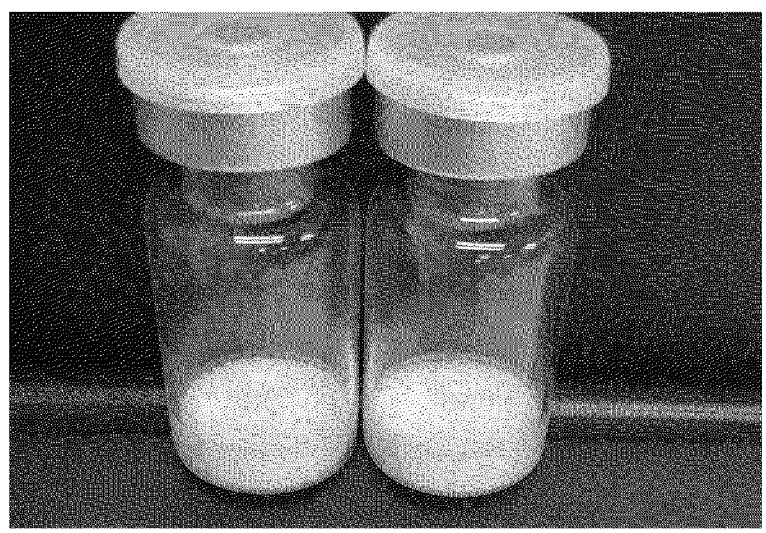
Figure 4G:
Figure 5:
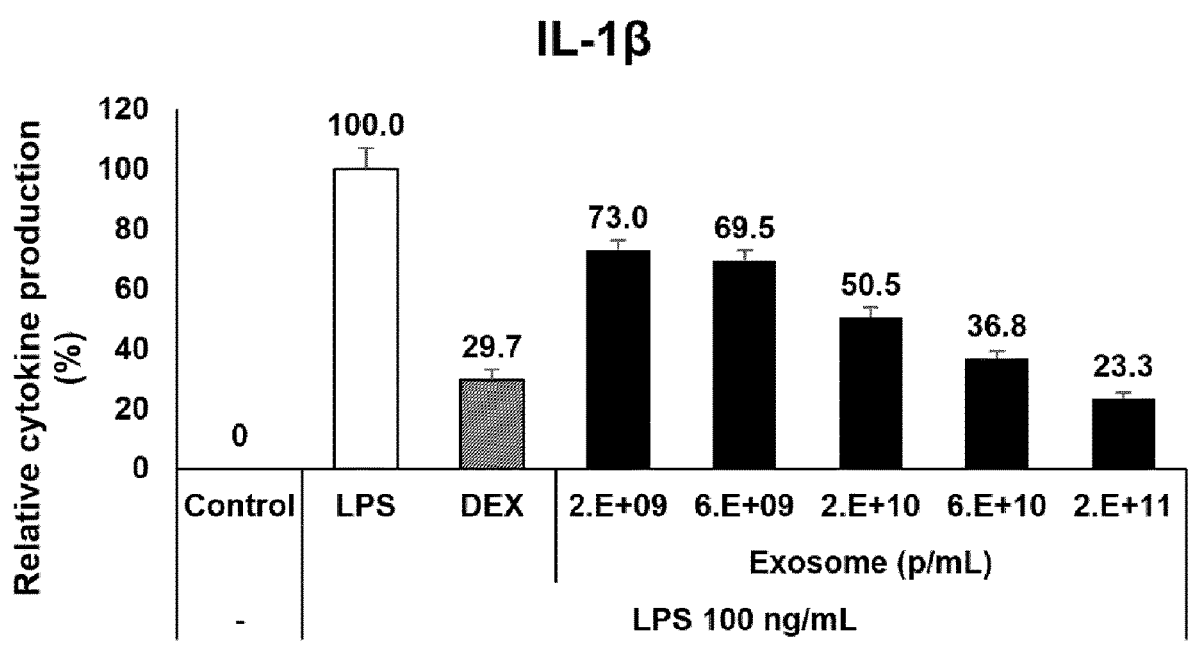
FIGS. 5 to 8 show the results of analyzing inflammatory cytokines using a multiplex panel.
Figure 6:
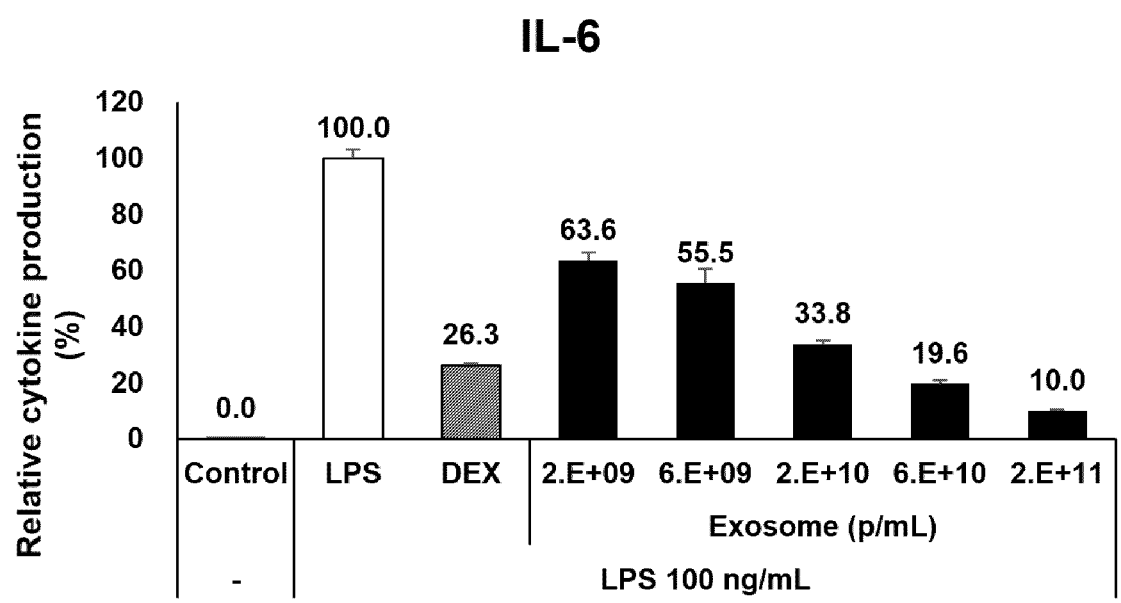
Figure 7:
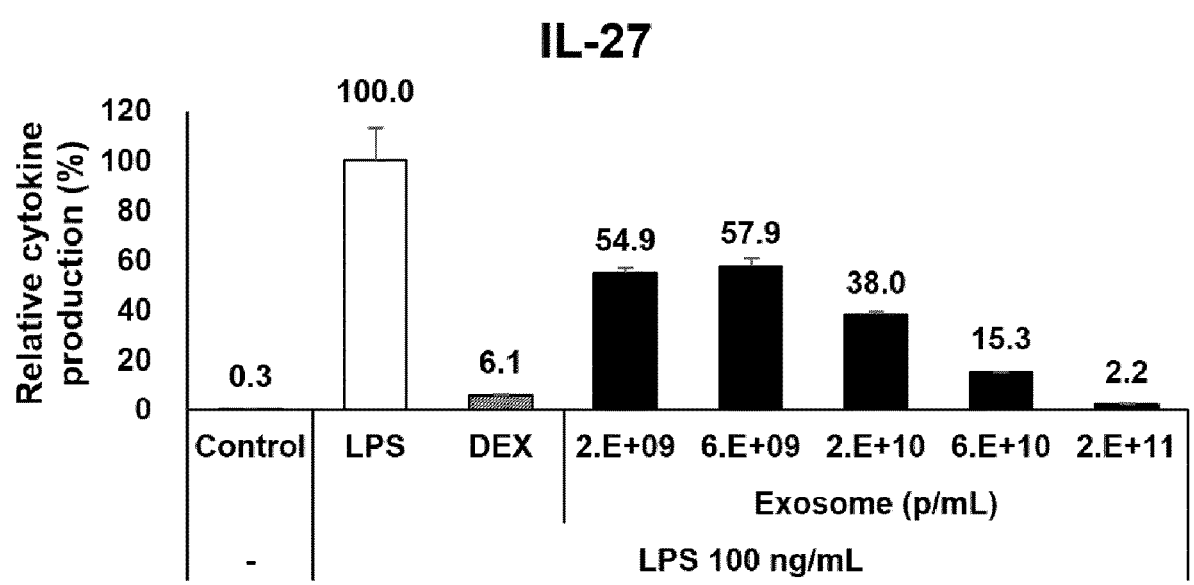
Figure 8:
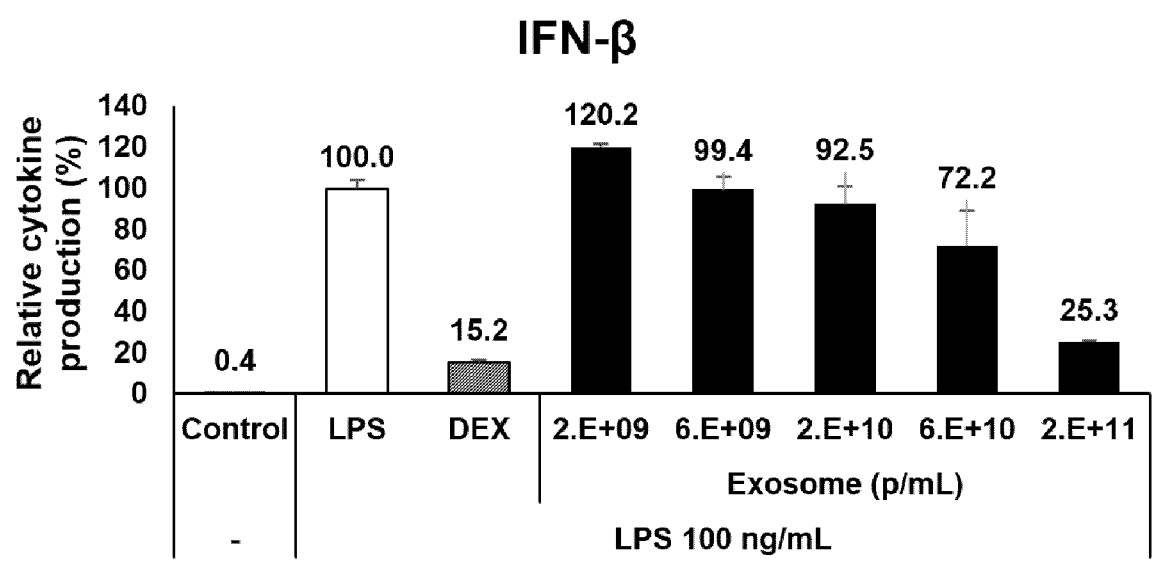
Figure 9:
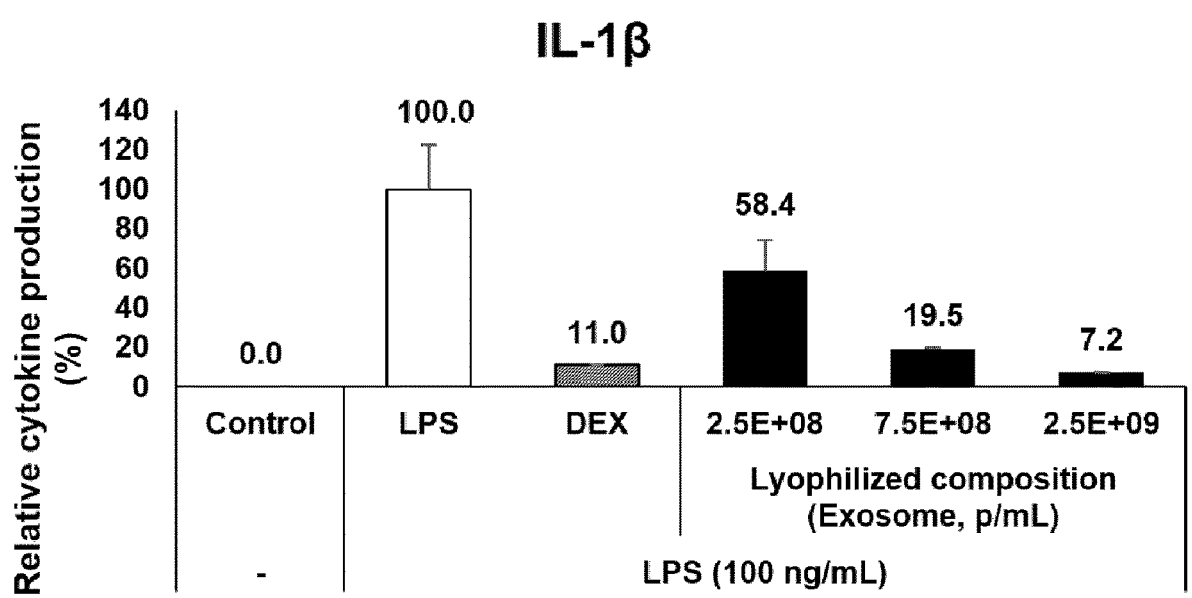
FIGS. 9 to 12 show the results of analyzing inflammatory cytokines using a multiplex panel.
Figure 10:
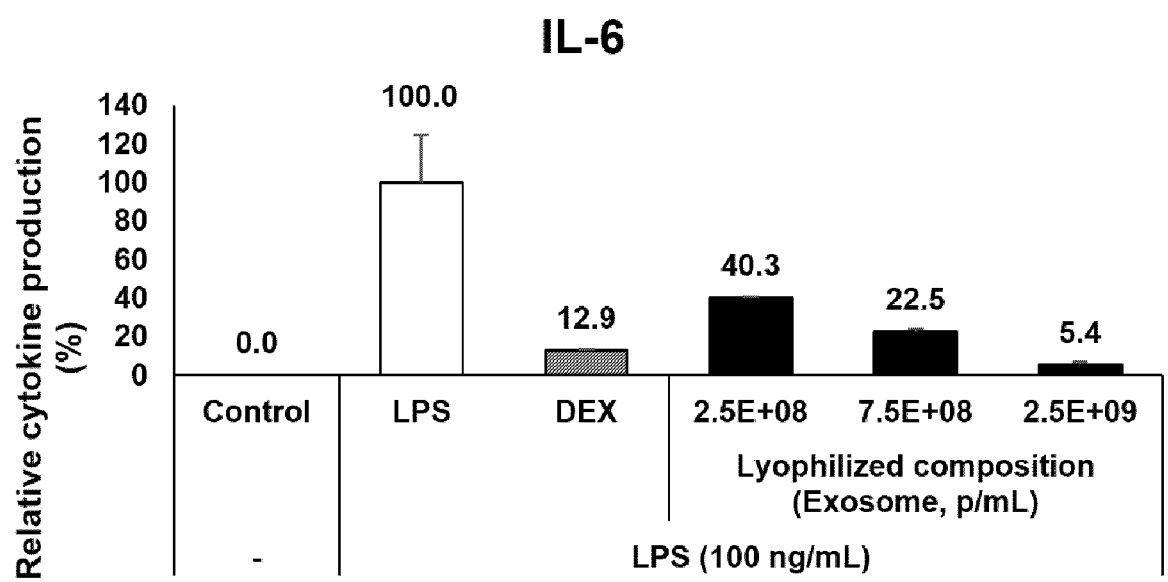
Figure 11:
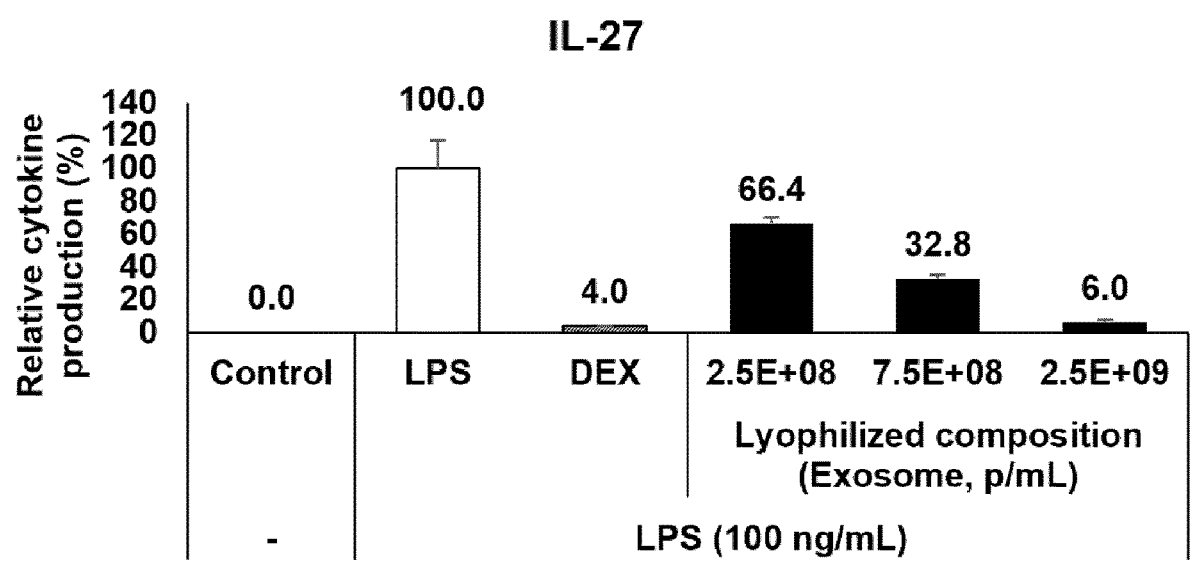
Figure 12:
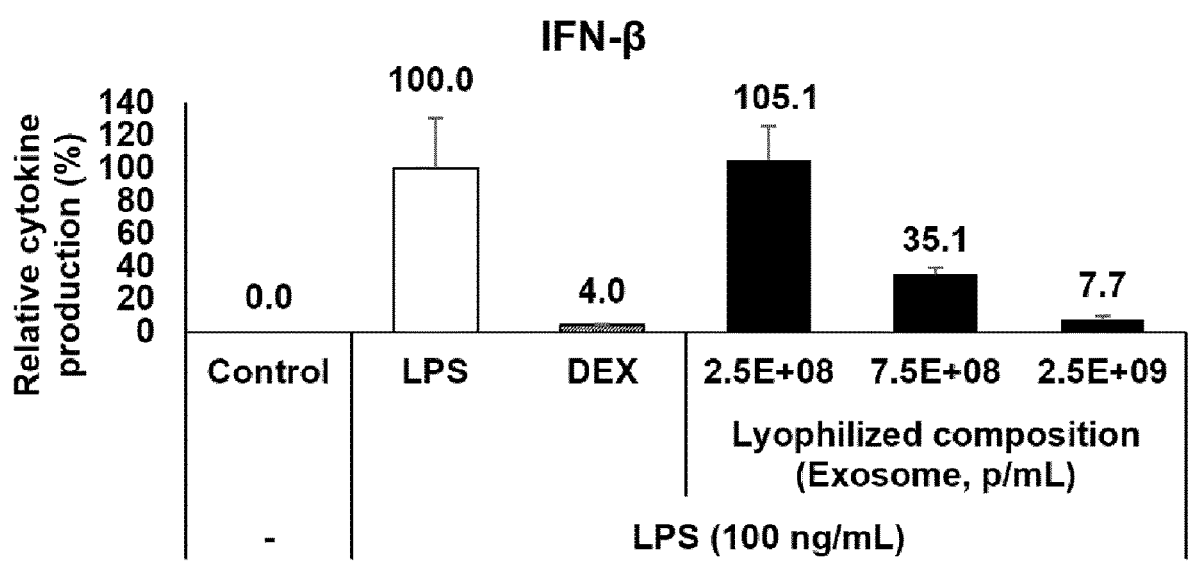

| | Composition of cryoprotectant components | | | | | | |
|---|---|---|---|---|---|---|---|
| | Mannitol | Trehalose | Methionine | Methionine + trehalose | Methionine + mannitol | Trehalose + mannitol | Methionine + mannitol + trehalose (present invention) |
| Evaluated score | 1 | 1 | 4 | 3 | 4 | 2 | 5 |
| FIGS. | FIG. 4A | FIG. 4B | FIG. 4C | FIG. 4D | FIG. 4E | FIG. 4F | FIG. 4G |

As shown in FIGS. 4A to 4G and Table 2 above, it can be seen that the product obtained by lyophilizing exosomes using the cryoprotectant having the combination of methionine, mannitol and trehalose has the best external appearance, however, the external appearances of the products obtained by lyophilizing exosomes using the one component or the combinations of the two components are poorer than that of the product of the present invention.

Example 6: Evaluation of Effect of Decreasing Inflammatory Cytokine Production

The effects of stem cell-derived exosomes (Example 2) and the lyophilized formulation (Example 5-1) of stem cell-derived exosomes upon decreases in inflammatory cytokine production in mouse macrophage RAW 264.7 cells were evaluated as follows.

RAW 264.7 cells were suspended in DMEM (Dulbecco Modified Eagle Medium; purchased from ThermoFisher Scientific) containing 10% FBS (Fetal Bovine Serum) and 1% penicillin-streptomycin, and then seeded into a 96-well plate at a density of $2.5 \times 10^4$ cells/well. Next, the cells were treated with difference concentrations (expressed as the number of particles per mL) of stem cell-derived exosomes (exosomes isolated and purified from conditioned media of stem cells) prepared in Example 2, and then cultured in an incubator at 37° C. under 5% $CO_2$ for 24 hours. In addition, in the same manner as the above-described method of treatment with stem cell-derived exosomes, RAW 264.7 cells were treated with aqueous solutions obtained and diluted by mixing the lyophilized formulation of stem cell-derived exosomes ($5 \times 10^9$ particles/vial) of Example 5-1 with a culture medium, and then the treated RAW 264.7 cells were cultured in an incubator at 37° C. under 5% $CO_2$ for 24 hours. Meanwhile, as a positive control, dexamethasone was used (indicated as DEX in FIGS. 5 to 12).

Thereafter, the RAW 264.7 cells were treated with 100 ng/mL of LPS (purchased from Sigma), and cultured in an incubator at 37° C. under 5% $CO_2$ for 24 hours, thus inducing activation of the cells.

After completion of the culture, the culture supernatant of the RAW 264.7 cells was collected, and the production of IL-1β, IL-6, IL-27 and IFN-β in the culture supernatant was measured using a mouse inflammation panel for LEGENDplex™ bead-based immunoassay (purchased from Biolegend) and NovoCyte Flow Cytometer (purchased from ACEA) in order to evaluate anti-inflammatory effects.

In addition, an MTT assay was performed to measure the change in cell viability caused by stem cell-derived exosomes, and the anti-inflammatory composition of the present invention, respectively, and to normalize the cytokine production therethrough. After the completion of culture, the culture medium of the RAW 264.7 cells was replaced with a DMEM medium containing 0.5 mg/mL of thiazolyl blue tetrazolium bromide (purchased from Sigma) and cultured for 1 hour. Next, the supernatant was removed in such a manner that the formazan formed at the bottom of the cell culture plate was not scattered. Subsequently, the formazan was dissolved by dimethyl sulfoxide (purchased from AMRESCO), and the absorbance was measured at 570 nm to determine the cell viability. In addition, the production of each of cytokines (IL-1β, IL-6, IL-27 and IFN-β) was normalized by the cell viability.

As shown in FIGS. 5 to 8, from the results of analyzing the inflammatory cytokines using the multiplex panel, it can be seen that when the RAW 264.7 cells were treated with the stem cell-derived exosomes before treating the cells with LPS, the LPS-induced production of each of IL-1β, IL-6, IL-27 and IFN-β decreased in a manner of depending on the concentration of the exosomes. In addition, as shown in FIGS. 9 to 12, from the results of analyzing the inflammatory cytokines using the multiplex panel, it can be seen that when the RAW 264.7 cells were treated with the anti-inflammatory composition of the present invention before treating the cells with LPS, the LPS-induced production of each of IL-1β, IL-6, IL-27 and IFN-β remarkably decreased in a manner of depending on the concentration of the anti-inflammatory composition.

From these results, it can be seen that the anti-inflammatory composition according to the present invention is able to stably maintain the anti-inflammatory efficacy of stem cell-derived exosomes contained therein as an active ingredient, and thus there is no possible change in the physical properties of exosomes during lyophilization, storage and distribution. In particular, when comparing the anti-inflammatory efficacy of not-lyophilized stem cell-derived exosomes (FIGS. 5 to 8) with the anti-inflammatory efficacy of the anti-inflammatory composition according to one embodiment of the present invention (FIGS. 9 to 12), it was confirmed that not-lyophilized stem cell-derived exosomes at a concentration of $2.0 \times 10^9$ particles/mL did not inhibit the production of the four inflammatory cytokines or merely inhibited their production by about 40%, whereas the anti-inflammatory composition according to one embodiment of the present invention inhibited the production of the four inflammatory cytokines by about 90% or more at a concentration of $2.5 \times 10^9$ particles/mL, which is similar to the concentration of not-lyophilized stem cell-derived exosomes. Therefore, the anti-inflammatory composition according to the present invention is able to stabilize stem cell-derived exosomes, which makes the composition commercially useful, and exhibit remarkable anti-inflammatory effect, as compared with not-lyophilized stem cell-derived exosomes. Thus, the anti-inflammatory composition according to the present invention is useful for the prevention, suppression, alleviation, amelioration or treatment of inflammatory diseases.

Although the present invention has been described with reference to the embodiments, the scope of the present invention is not limited to these embodiments. Any person skilled in the art will appreciate that various modifications and changes are possible without departing from the spirit and scope of the present invention and these modifications and changes also fall within the scope of the present invention.

We claim:

1. An anti-inflammatory composition comprising:
   a lyophilized formulation of stem cell-derived exosomes comprising stem cell-derived exosomes, and a combination of methionine, mannitol and trehalose as a cryoprotectant; and
   a diluent;
   wherein the diluent comprises water for injection, physiological saline, phosphate buffered saline, purified water, or deionized water; and
   wherein the diluent further comprises hyaluronic acid or hyaluronate.

2. The anti-inflammatory composition of claim 1, wherein the composition is prepared as a suspension.

3. The anti-inflammatory composition of claim 1, wherein the composition is a pharmaceutical composition, a cosmetic composition, or a skin external preparation.

4. The anti-inflammatory composition of claim 3, wherein the pharmaceutical composition is an injectable formulation.

5. A method for alleviating, ameliorating or treating inflammation of skin of a subject in need thereof, the method comprising step of:
(a) treating an inflammatory area in the skin of the subject with an anti-inflammatory composition, wherein the anti-inflammatory composition comprises a lyophilized formulation of stem cell-derived exosomes which comprises stem cell-derived exosomes and a combination of methionine, mannitol and trehalose as a cryoprotectant.

6. The method of claim 5, wherein the anti-inflammatory composition further comprises a diluent.

7. The method of claim 6, wherein the diluent comprises water for injection, physiological saline, phosphate buffered saline, purified water, or deionized water.

8. The method of claim 7, wherein the diluent further comprises hyaluronic acid or hyaluronate.

9. The method of claim 6, wherein the anti-inflammatory composition is prepared as a suspension.

10. The method of claim 6, wherein the anti-inflammatory composition is an injectable formulation.

11. The method of claim 6, wherein the anti-inflammatory composition is administered to the skin by microneedling, iontophoresis, or injection.

12. The method of claim 5, further comprising steps of:
(b) performing iontophoresis by allowing a microcurrent to flow through the skin treated with the anti-inflammatory composition; and
(c) delivering the anti-inflammatory composition inside the skin by the microcurrent.

13. The method of claim 12, wherein the anti-inflammatory composition is used in at least one form selected from the group consisting of a patch, a mask pack, a mask sheet, a cream, a tonic, an ointment, a suspension, an emulsion, a paste, a lotion, a gel, an oil, a spray, an aerosol, a mist, a foundation, a powders, and an oilpaper.

14. The method of claim 13, wherein the anti-inflammatory composition is applied to or soaked in at least one surface of the patch, the mask pack, or the mask sheet.

15. The method of claim 14, wherein the step (a) is performed by:
(a1) applying the anti-inflammatory composition directly to the skin; or
(a2) contacting or attaching the mask pack, the mask sheet or the patch, which has the anti-inflammatory composition applied thereto or soaked therein, to the skin; or sequentially performing (a1) and (a2).

16. The method of claim 15, wherein the step (b) is performed by contacting or attaching an iontophoresis device to the skin.

17. The method of claim 16, wherein the iontophoresis device comprises at least one battery selected from the group consisting of flexible batteries, lithium-ion secondary batteries, alkaline batteries, dry cells, mercury batteries, lithium batteries, nickel-cadmium batteries, and reverse electrodialysis batteries.

18. A method for alleviating, ameliorating or treating inflammation of skin of a subject in need thereof, the method comprising step of:
(a1) applying an anti-inflammatory composition to the skin of the subject;
or (a2) contacting or attaching a patch, a mask pack or a mask sheet, which has the anti-inflammatory composition applied thereto or soaked therein, to the skin; or
(a3) sequentially performing (a1) and (a2),
wherein the anti-inflammatory composition comprises a lyophilized formulation of stem cell-derived exosomes which comprises stem cell-derived exosomes and a combination of methionine, mannitol and trehalose as a cryoprotectant.

19. The method of claim 18, wherein the anti-inflammatory composition further comprises a diluent.

20. The method of claim 19, wherein the diluent comprises water for injection, physiological saline, phosphate buffered saline, purified water, or deionized water.

21. The method of claim 20, wherein the diluent further comprises hyaluronic acid or hyaluronate.

22. The method of claim 18, wherein the anti-inflammatory composition is prepared as a suspension.

23. The method of claim 18, further comprising step (b) removing the patch, the mask pack or the mask sheet from the skin after step (a2) or (a3), and applying the anti-inflammatory composition to the skin.

24. A method for alleviating, ameliorating or treating inflammation of skin of a subject in need thereof, the method comprising
administering a therapeutically effective amount of an anti-inflammatory composition to the subject, wherein the anti-inflammatory composition comprises a lyophilized formulation of stem cell-derived exosomes which comprises stem cell-derived exosomes and a combination of methionine, mannitol and trehalose as a cryoprotectant.

25. The method of claim 24, wherein the anti-inflammatory composition further comprises a diluent.

26. The method of claim 25, wherein the diluent comprises water for injection, physiological saline, phosphate buffered saline, purified water, or deionized water.

27. The method of claim 26, wherein the diluent further comprises hyaluronic acid or hyaluronate.

28. The method of claim 24, wherein the anti-inflammatory composition is prepared as a suspension.

* * * * *